(12) United States Patent
Cole

(10) Patent No.: US 6,521,464 B1
(45) Date of Patent: Feb. 18, 2003

(54) METHODS AND APPARATUS FOR PREVENTING SAMPLE LOSS

(75) Inventor: Michael Cole, Saxmundham (GB)

(73) Assignee: Genevac Limited, Ipswich (GB)

( * ) Notice: Subject to any disclaimer, the term of this patent is extended or adjusted under 35 U.S.C. 154(b) by 0 days.

(21) Appl. No.: 09/550,694

(22) Filed: Apr. 17, 2000

(30) Foreign Application Priority Data

| Apr. 17, 1999 | (GB) | 9908746 |
| Jun. 19, 1999 | (GB) | 9914332 |
| Aug. 12, 1999 | (GB) | 9918915 |

(51) Int. Cl.[7] .............................................. G01N 1/00
(52) U.S. Cl. ...................... 436/176; 436/183; 422/102; 422/99
(58) Field of Search ............................ 422/79, 99–107; 436/176, 183

(56) References Cited

U.S. PATENT DOCUMENTS

| 3,481,712 A | * | 12/1969 | Bernstein et al. | 215/227 |
| 3,923,969 A | * | 12/1975 | Baukal et al. | 424/469 |
| 4,683,058 A | * | 7/1987 | Lyman et al. | 210/515 |
| 5,118,858 A | * | 6/1992 | Williams et al. | 568/67 |
| 5,620,662 A | * | 4/1997 | Perlman | 422/102 |
| 5,725,832 A | * | 3/1998 | Gundelsheimer | 422/102 |

FOREIGN PATENT DOCUMENTS

| JP | 11155593 | 6/1999 |
| WO | WO 98/33052 | 7/1998 |

* cited by examiner

Primary Examiner—Jill Warden
Assistant Examiner—Yelena G. Gakh
(74) Attorney, Agent, or Firm—Lee, Mann, Smith, McWilliams, Sweeney & Ohlson

(57) ABSTRACT

A reduction of sample loss from a container open to atmosphere, and including liquid trifluoroacetic acid (TFA), is carried out by a variety of methods each of which reduces creep of TFA up the walls of the container. In one method, particularly applicable to microtitre plates, each container or well is sealed by a cap which is retained by a strap (FIGS. 4 and 5). In another method the top of the container is formed with a downwardly pointing entrance tube, in the form of an unspillable inkwell (FIG. 2), where the container is a screw top vial, the entrance tube is sealed around the top of the neck of the vial (FIG. 9b).

6 Claims, 7 Drawing Sheets

TFA liquid creeping up the inner walls of its container

Unspillable inkwell shaped tube top

Continuous vapour removal

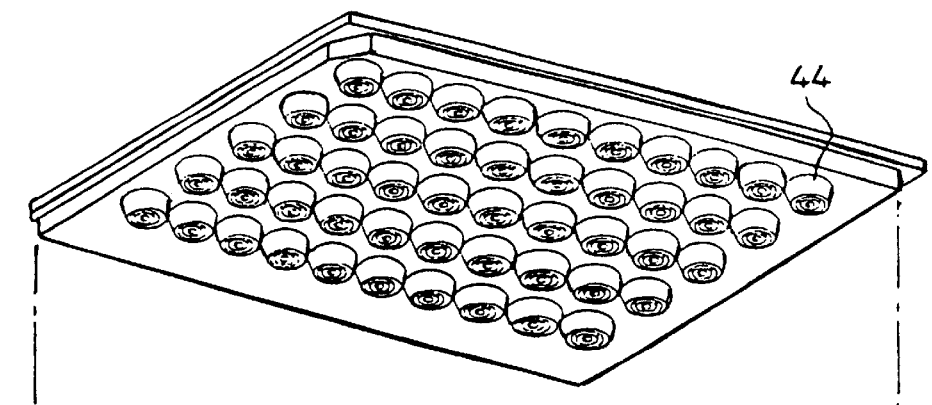
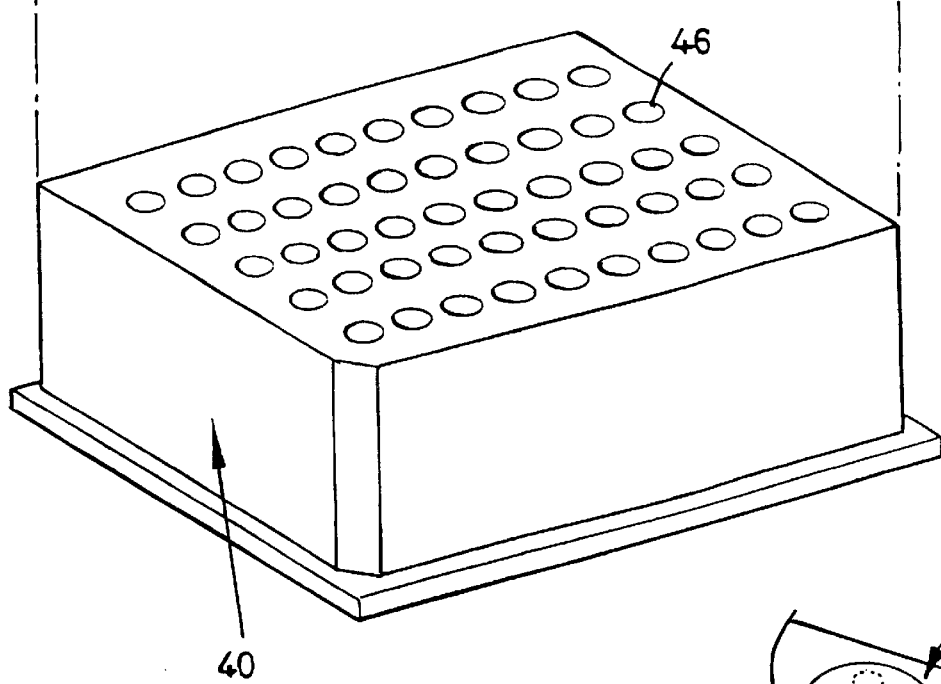
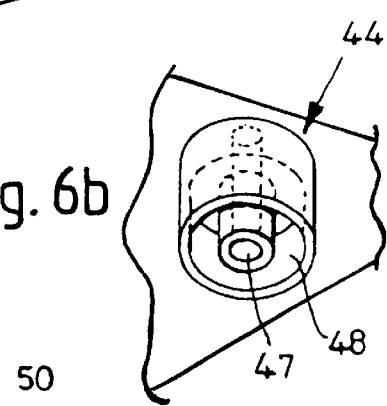
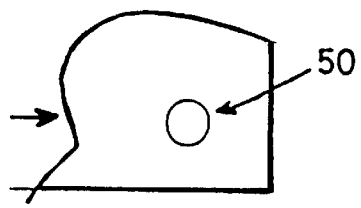
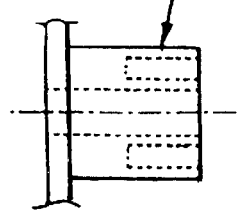
Fig. 6a
Fig. 6b
Fig. 6c
Fig. 6d

METHODS AND APPARATUS FOR PREVENTING SAMPLE LOSS

FIELD OF THE INVENTION

This invention concerns techniques for preventing sample loss from containers open to atmosphere, especially loss of liquid trifluoroacetic acid (TFA) due apparently to anomalous surface properties which, under certain circumstances, cause the liquid TFA and any solids in solution therein to creep up the walls of a container and even right out of, and down the external walls of a container.

BACKGROUND TO THE INVENTION

TFA has been found to creep in this way in partially filled tubes open to the atmosphere at temperatures of around 20° C.

This can be highly undesirable, particularly when it is used for cleaving synthesised molecules from resin beads in solid phase synthesis of organic molecules. In this application TFA, usually mixed with an organic solvent such as dichloromethane, is added to resin beads in a tube or other container, for example a microtitre plate, (container) on which organic molecules have been synthesised. These molecules are all attached, at some point on each molecule, to the beads and the TFA breaks the bond, which attaches them to yield the required molecule in solution in the TFA/solvent mix. The next step in the process is usually evaporation of the TFA/solvent mix (TFA mix) to yield the newly synthesised compound. If some of the TFA mix creeps out of the sample container it will take some of the compound with it and that amount of compound is normally lost. As synthesising such compounds can be very expensive this is highly undesirable. In multi-sample holders, such as microtitre plates, compound escaping from one well can migrate into an adjacent well causing cross-contamination.

SUMMARY OF THE INVENTION

According to one aspect of the present invention, creep of TFA may be reduced by the addition of dichloromethane to a sample so that the TFA content of the liquid is reduced to 20% or less.

According to another aspect of the invention, creep of TFA may be reduced by the addition of 10% water or another liquid to the sample. In general creep will be reduced but the compound may not cleave from its resin in dilute solutions of TFA.

It is of course a prerequisite that any added liquids will not react with the compound.

Creep of TFA liquid seems only to occur on surfaces which are in contact with concentrated TFA vapour. This form of creep may well occur in other liquids when in contact with concentrated vapour of the same liquid, and according to another aspect of the invention dichloromethane or water or other liquids may be added to reduce such creep of other liquids.

Five methods have been devised for preventing or minimising the effect of this phenomenon. In all these methods it is preferable though not essential to have a dry inert gas eg dry nitrogen, rather than air, filling that part of the container not filled with TFA mix. This is because the strong affinity of TFA for the water in atmospheric air causes other problems.

In a first method, the top of the sample container is sealed as soon as the TFA mix has been added. The TFA vapour, which is heavier than air, evaporates to form a layer over the liquid surface but cannot fill the rest of the empty space above the liquid because it cannot displace the air or other gas in the sample container above the vapour. If the TFA mix only partially fills the container the liquid film on the sides of the container will not rise to the top of the container. The sample containers need to be unsealed in a centrifugal evaporator only after they are subjected to enough centrifugal force (in the region of a few hundred G) to prevent creep when the sealing caps or closures have been removed.

In a second method a container is employed in which the top is formed with a central tubular entrance in the form of an unspillable inkwell. The container is filled with TFA mix to a level below that of the lowest level of the central downward pointing tubular entrance of the container. TFA vapours will occupy the central entrance tube up to a level slightly above that of the lower end of the entrance tube, but can go no further if gas or air, displaced in the container by the TFA vapour, is trapped in the annular space around the tubular entrance tube, below the upper wall of the container surrounding inwardly directed the tube. There is therefore no continuous path in the inside surface of the container wall, in contact with TFA vapour, up which the TFA liquid mix can creep. This solution to the problem is more convenient in that there is no need to cap the container after filling it with resin beads, TFA mix or other chemicals, so that there is no cap to be removed when the samples are to be evaporated as when rotated in a vacuum chamber.

The ring shaped top can be formed as an integral part of the tube or well, or a cap fitted to a straight tube, or a small cap fitted to each of the openings in a microtitre plate. In screw top vials (eg see FIG. 9a) the ring can be formed by inserting a short tube and sealing it hermetically (FIG. 9b).

In a third method the container is filled with an inert gas having a higher density than TFA vapour (such as sulphur hexafluoride) shortly before, or shortly after, adding the TFA to the container. The heavy gas is not so readily displaced as air or nitrogen and will prevent or delay the TFA vapour filling the container which, in turn, will prevent the liquid TFA mix from reaching the top of the container or delay the process sufficiently to prevent sample loss or cross-contamination arising from creep of TFA mix.

In a fourth method, the TFA vapour is continuously removed and replaced with air or an inert gas such as nitrogen. In this arrangement a tube may be inserted into the container to a position at which its lower open end is just above the TFA mix, and the top end of the tube is connected to a pump or reduced pressure collecting device, so as to suck out the TFA vapour as soon as it reaches the level of the lower end of the tube. A gas such as nitrogen or air, is admitted to the top of the container to compensate for the loss of gas volume caused by the removal of the TFA mix vapour. Under these conditions the TFA mix liquid rises as far as the lower end of the tube but no further, and again a barrier exists, above that level, up which the TFA will not in general creep.

This method has the added advantage that it promotes rapid evaporation of the TFA mix and can be used both as a method of preventing TFA creep and of evaporating the TFA mix. If this method is used to prevent creep, the suction flow rate is kept to the minimum required to reduce evaporation during the time the TFA mix is required to be in contact with the resin. For evaporation after the required period, the flow rate can be increased to give rapid evaporation.

In essence therefore, according to the invention, the phenomenon of liquid creep up the wall of a vessel containing the liquid, is prevented by creating a continuous region on the inside surface of the vessel which cannot come into contact with the liquid vapour which exists above the surface of the liquid in the vessel.

In a fifth method measures are taken to ensure that the whole of the surface of the container is already coated in liquid TFA mix but of a mix not containing the solid material in solution in the sample. Because the surface above the TFA mix sample level is already coated in TFA mix there is no tendency for further TFA mix containing the sample to creep up the walls.

This situation can be created, for instance, by spraying pure TFA mix onto the surface of the container before or after the containers are filled with sample. If the sample needs to remain in contact for a considerable time before evaporation can take place it may be necessary to repeat the application of pure TFA mix so that the walls above the sample do not dry out and draw up the TFA mix sample.

In most procedures for solid phase synthesis the TFA mix is evaporated in a centrifugal evaporator after it has achieved the required cleavage of the compound from the resin. Once sufficient centrifugal force has been applied to the sample, the tendency of the TFA mix to creep up the walls of the container is suppressed. The requirement to prevent or delay creep, so that the sample does not migrate out of its container, is therefore during the period prior to centrifuging, and until sufficient centrifugal force has been applied to the sample to prevent creep. If no such precautions are taken, creep to the top of the container can occur in a few minutes—typically 10–15 minutes. Samples frequently have to be held for considerably longer periods before they can be evaporated, and in this period they are usually held outside a centrifugal evaporator.

If a heavy gas such as sulphur hexafluoride is used to delay creep it may be necessary to repeat the action of filling the space above the TFA mix with the heavy gas several times if there is an appreciable delay in applying centrifugal force to the sample after adding the TFA mix.

Sometimes the TFA mix must be left in contact with the sample for an hour or longer to allow the cleavage action to be completed, before evaporation can be started.

In accordance with another aspect of the invention it may be desirable to apply centrifugal force to a container filled or partially filled with a liquid sample such as TFA, without applying vacuum, until the sample is ready to be evaporated.

Alternately in accordance with another aspect of the invention the samples liable to creep may be stored in a chamber filled with a heavy gas, possibly under a positive pressure (ie greater than atmospheric pressure) so that the possibility of the gas being displaced by TFA mix vapour is reduced.

If creep is prevented by sealing the containers after filling with TFA mix, means is required for removing the sealing means when evaporation of the mix is required. The seals are preferably removed after the application of centrifugal force, but this will normally only occur after the samples are in a vacuum chamber and are being rotated at considerable speed. This situation makes it difficult to remove the seals, and seals which blow off can interfere with the rotating samples.

One possible method is to use sealing caps which can be pushed into the tops of the containers manually or by automatic mechanical means, and held in place by a friction fit sufficient to provide a good seal, but not enough to prevent the caps being pushed out of the containers by a pressure difference of a fraction of an atmosphere as can be caused by the application of a partial vacuum to the exterior of the tubes. The pressure difference arises because the containers are normally sealed under atmospheric pressure although a higher pressure could be used at a cost of increased complexity in the apparatus.

Caps to seal microtitre plates are commercially available either in strips or as individual caps or as complete blocks to cover all 96 wells in a 96 well microtitre plate. These could be retained by means of small straps so that they would fly out of the wells on application of a partial vacuum but be retained close to the wells. The caps may partially block the tops of the wells, but this will not interfere with evaporation.

Similar capping and strapping arrangements could be applied to tubes, and arrays of tubes.

According to another aspect of the invention, particularly applicable to microtitre plates or arrays of tubes, centrifugal force is used to remove the sealing caps. In this arrangement sealing caps, which match the arrangement of the wells in the microtitre plate, are secured to a rigid backing plate and pins or rods extend from the backing plate into holes in the microtitre plate (eg see FIG. 5a).

When the wells in the plate have been filled, the backing plate is fitted to the microtitre plate. The caps align with and seal the wells, and the pins project through and a short distance, typically about 5 mm, beyond the bottom of the microtitre plate.

The fit between the pins and the holes in the plate, or between the caps and the wells, or both, is such that the weight of the plate is insufficient alone to cause the plate to drop relative to the backing plate, when the plate is located on a horizontal surface and stood on the ends of the protruding pins.

After placement in a centrifugal evaporator and spun, centrifugal force added to the weight of the microtitre plate will release and break the seals, and cause the plate to slide down the pins thereby creating a gap around the top of each of the wells, which will allow evaporation to take place.

A similar mechanism can be applied to an individual tube, or to an array of tubes.

BRIEF DESCRIPTION OF THE DRAWINGS

The invention will now be described by way of example, with reference to the accompanying drawings in which:

FIGS. 6(a) to 6(d) show a modification of a microtitre plate;

DETAILED DESCRIPTION OF THE DRAWINGS

Figure 1:
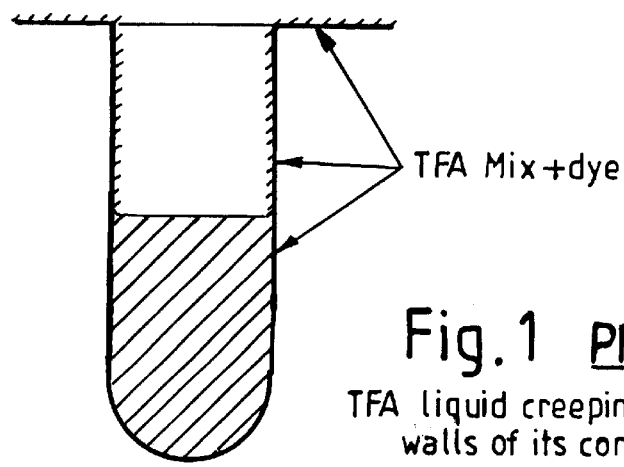
FIG. 1 is a side view of a conventional tube containing a TFA mix.

Referring first to FIG. 1, if a tube or well in a microtitre plate is partially filled with TFA mix containing more than 20% TFA, it will gradually creep up the inside of the container walls and onto the top of the container. This phenomenon occurs in glass, PTFE and polypropylene containers, and probably will also occur in containers made of other materials. It can be made visible by dissolving a coloured substance or dye such as menthyl orange in the TFA mix. The TFA mix vapour is highly volatile and evaporates from the surface displacing air (which is less dense) and bringing TFA vapour into contact with the sides of the container above the liquid. This appears to allow the liquid to creep up the container to the level of the TFA vapour.

Figure 2:
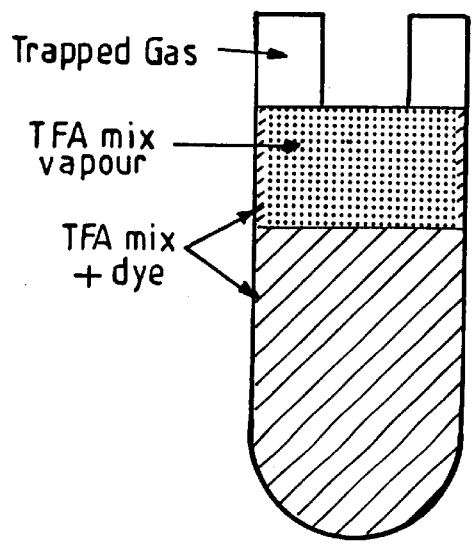
FIG. 2 is a similar view showing an embodiment of the invention incorporating an "unspillable inkwell"

As shown in FIG. 2, a ring of internal chamber wall can be kept free of vapour, by using a container having the re-entrant top characteristic of the so-called unspillable ink well. Here the layer of vapour traps gas (typically air or nitrogen) in the circular region around the re-entrant top, and this prevents the liquid creeping up and around the inside of the vessel.

Figure 3:
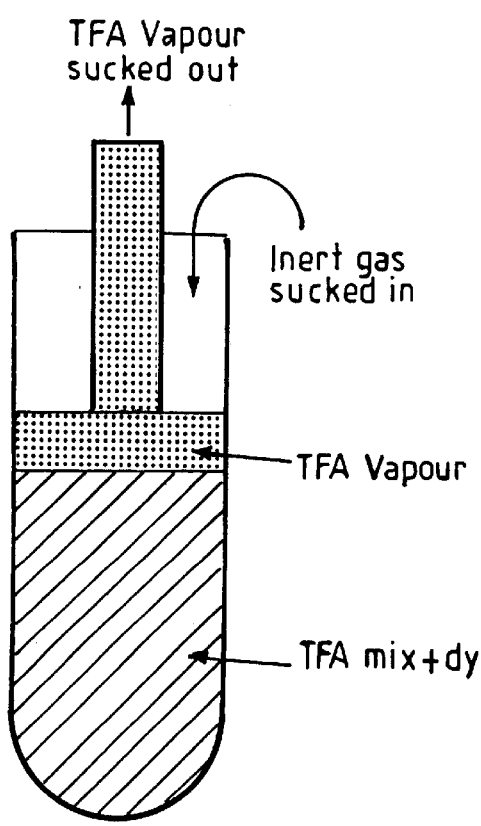
FIG. 3 shows another embodiment of the invention.

In FIG. 3, vapour above a volume of TFA mix in a conventional open-ended container, such as a tube or microtitre well, is continuously evacuated through a tube which protrudes down into the container to a point above the level of the TFA. An inert gas is drawn in to the top of the container from the space above the container which itself is supplied with the said inert gas in sufficient quantity to replace that which is removed by the evacuation tube. The absence of vapour in the upper region of the container prevent creep from occurring above the level of the vapour layer between the TFA mix and the lower end of the central evacuating tube.

Figure 4:
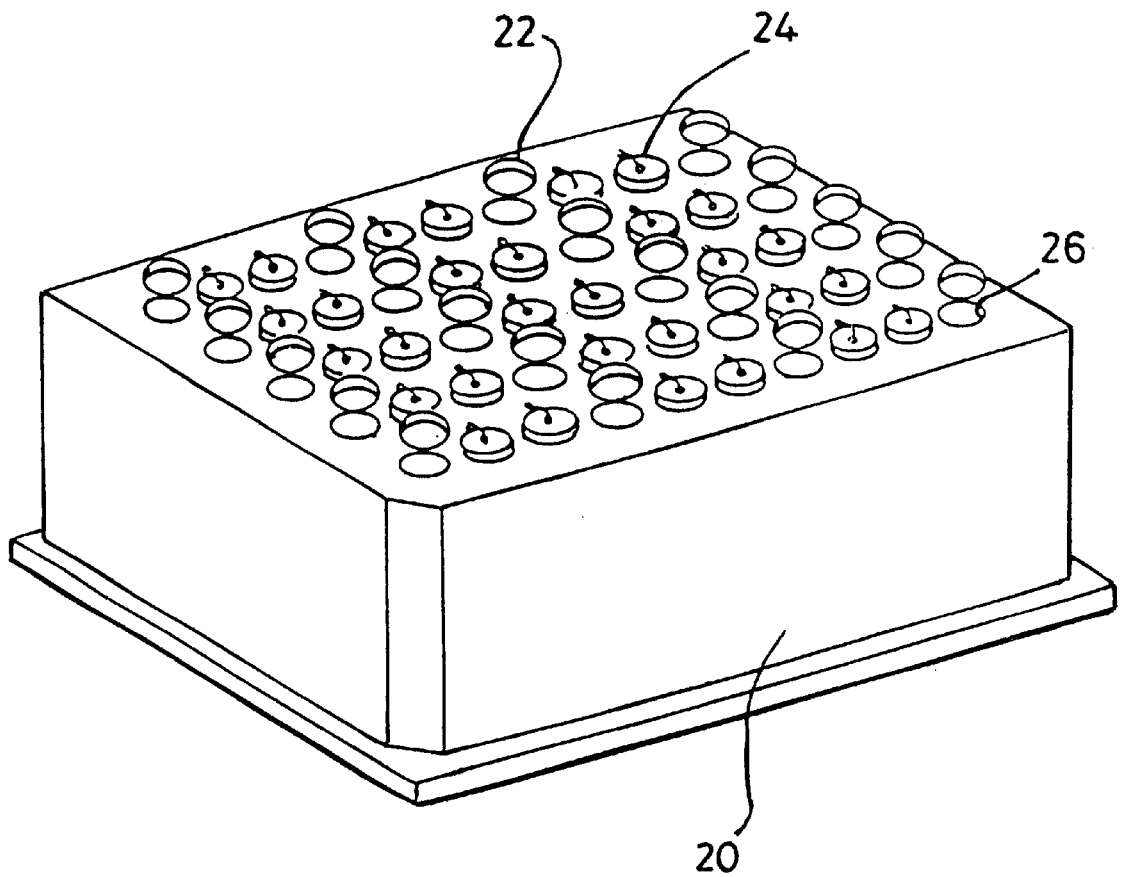
FIG. 4 shows a perspective view of a microtitre plate having sealing caps in accordance with the invention.

FIG. 4 shows a conventional microtitre plate 20 having individual caps 22, strapped to the closure plate by flexible straps 24 adjacent each well 26, and adapted to be fitted over or into the top of each well to seal it after filling with TFA mix. Under an appropriate pressure differential the caps will be lifted off the wells to open them and permit evaporation, but will remain attached to the plate by means of the flexible straps.

Figure 5A:
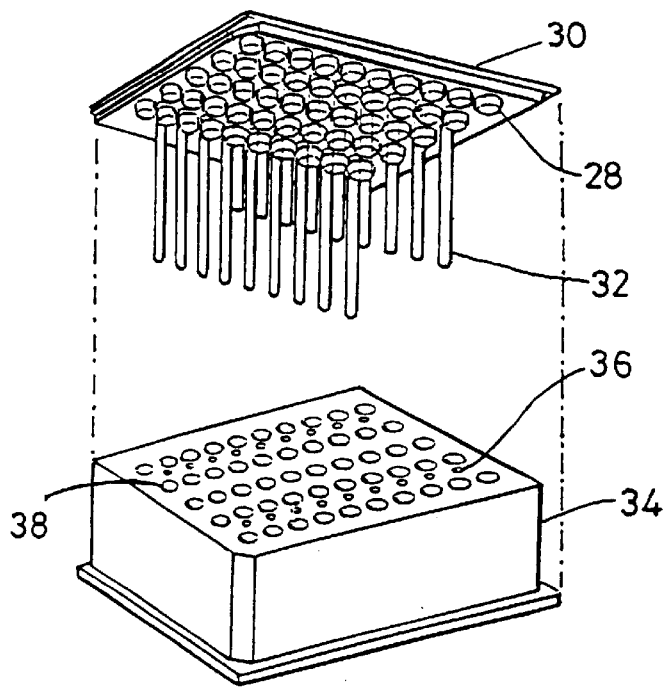
FIGS. 5(a) to 5(c) show an alternative microtitre plate at different stages.
Figure 5B:
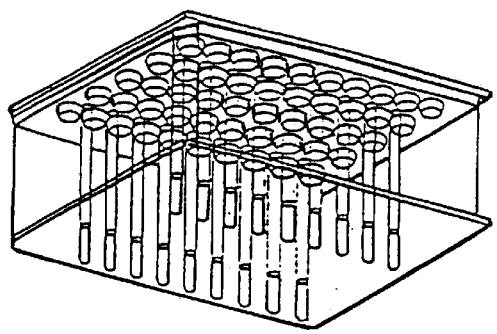
Figure 5C:
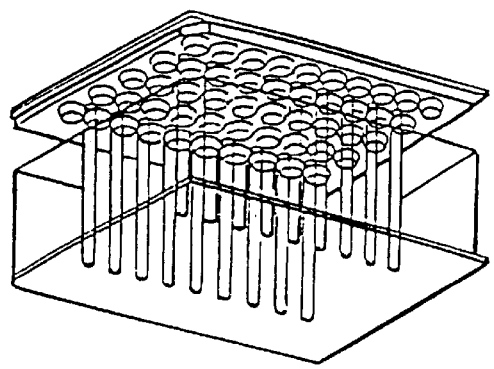

In an alternative embodiment shown in FIG. 5, centrifugal force is used to remove the sealing caps. As can be seen in FIG. 5(a), each sealing cap 28 is secured to a closure plate 30 to which are attached push rods or pins 32. FIG. 5a also illustrates a microtitre plate 34 with extra holes 36 through which the pins 32 can slide when the closure plate 30 is placed on top of the microtitre plate to seal the wells 38. The microtitre plate 34 with the closure plate 30 in position will stand on the protruding pins which extend from the closure plate and through the microtitre plate. After filling the wells with the TFA mix, the closure plate is pressed down onto the microtitre plate so that the caps 28 seal the wells, and the pins will then project a short distance beyond the underside of the microtitre plate, as shown in FIG. 5(b). When the sealed microtitre plate is placed in a swivelling bucket of an evaporator, the weight of the plate (ie its mass) is sufficient to separate it from the closure plate and open up the wells to the vacuum. Thus when the evaporator rotor is rotated the buckets swivel to the horizontal position (not illustrated), and the centrifugal forces on the microtitre plate increase to a point at which it is sufficient to separate the two plates and break the seals, exposing the wells to the vacuum, as illustrated in FIG. 5(c).

Referring now to FIGS. 6, the principle of a re-entrant top feature, shown in FIG. 2 as applied to an individual tube, can equally be applied to multiple sample holders, eg microtitre plates.

FIG. 6(a) shows a conventional microtitre plate 40 and a lid or closure plate 42 for fitting thereover. As more clearly shown in the enlarged scrap view of FIG. 6(b), a re-entrant sealing cap 44 is secured to the underside of the closure plate 42 at each position corresponding to a well 47 in the microtitre plate. As with the embodiment of FIG. 2, the cap 44 has a central vented passage 46 and an annular recess 48 which acts to trap a layer of gas/TFA vapour when the cap is pushed down firmly into a respective well 46.

Alternatively, as shown in FIGS. 6(c) and 6(d), a similar sealing cap 50 can either be pushed into each well 46 of a conventional microtitre plate 40 or can be moulded therein. In the former case, and with that of FIGS. 6(a) and (b), it is important that each sealing cap makes an air-tight seal against the inside wall of the respective well.

Figure 7:
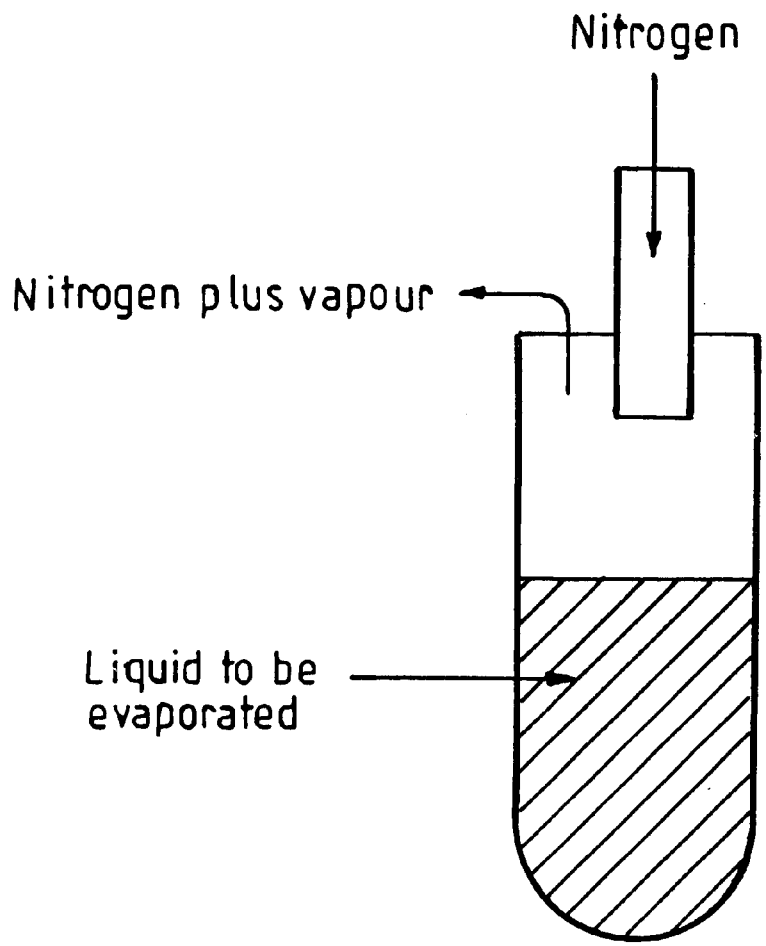
FIG. 7 shows a container operating under a known nitrogen blow-down process.

The cap 44 may instead be sealed, e.g. by ultrasonic welding, to the top face of the microtitre plate 40 around the perimeter of each well 47. Evaporation of TFA mix or other volatile liquids by directing a stream of air or an inert gas such as nitrogen onto the surface of the liquid (see FIG. 7) is a well known process and widely used for evaporating volatile liquids. It suffers from the disadvantage that large volumes of the inert gas, contaminated with the vapour, must be disposed of. This can be expensive if the liquid is inflammable or toxic.

Figure 8:
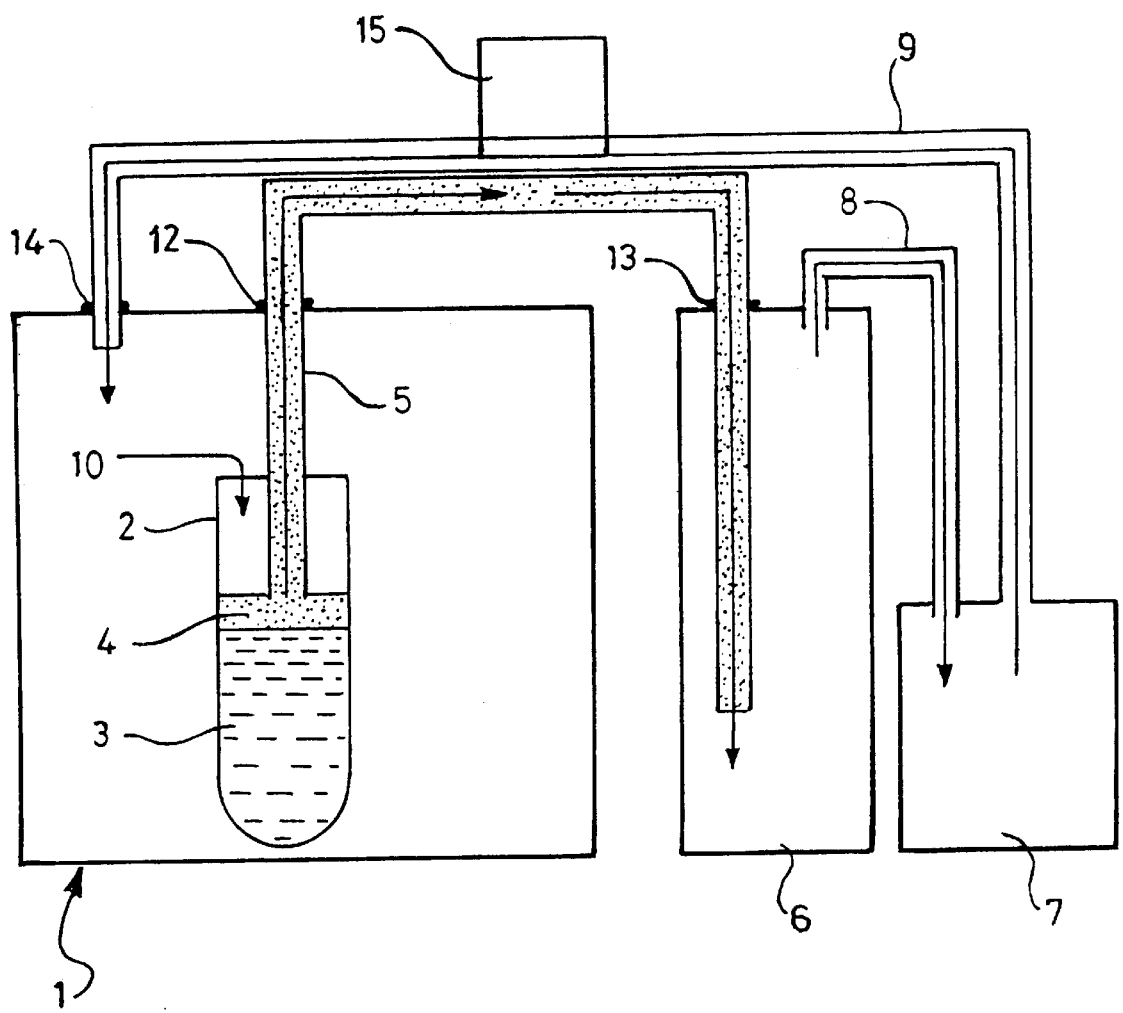
FIG. 8 shows an improvement in the process of FIG. 7.
Figure 9A:
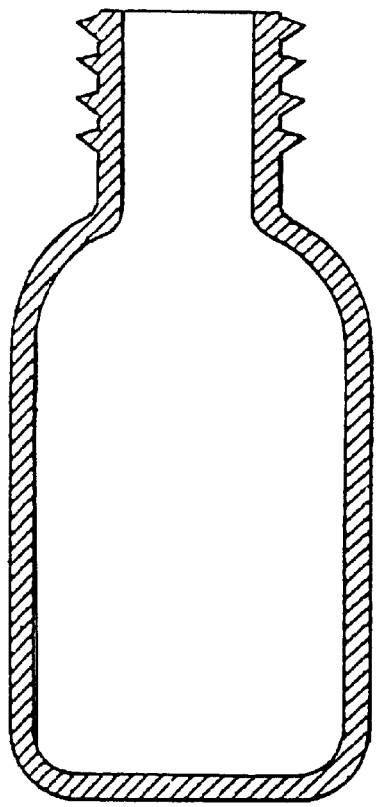
FIG. 9(a) and (b) show how the feature of FIG. 2 can be applied to a screw top vial.
Figure 9B:
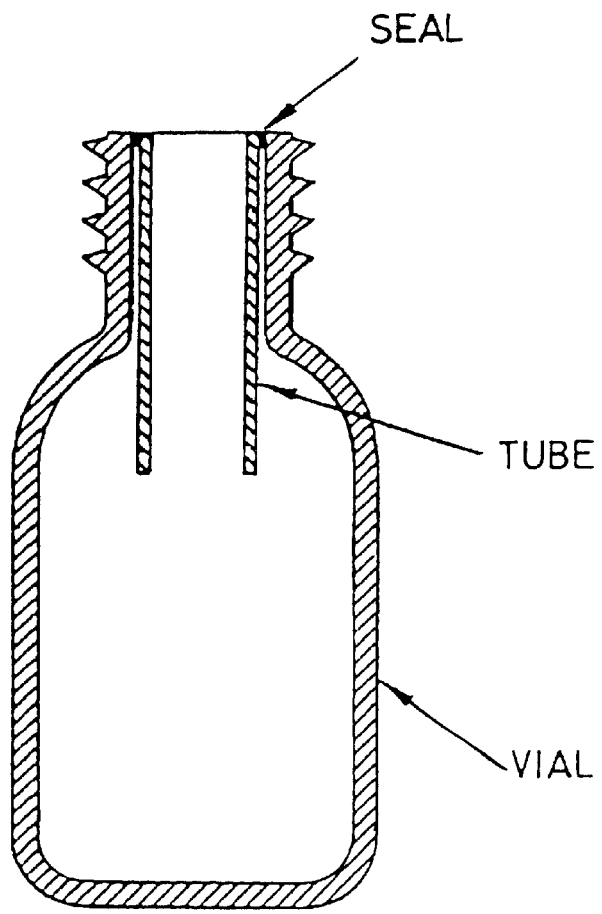

The opposite process is illustrated in the embodiment of FIG. 8, in which gas, rich in vapour from near the surface of the liquid, is continuously removed. This process is at least as fast as the known process and allows much easier collection of the toxic material.

As illustrated in FIG. 8, the liquid sample 3 is contained in a tube 2 inside a sealed chamber 1. A suction tube 5 is placed with one end 11 in the tube 2 and above the sample 3. This tube passes through the chamber 1 through a sealing means 12 and through a further sealing means 13 into a sealed refrigerated condensing vessel 6.

A further tube 8 connects the refrigerated condensing vessel 6 to a pump 7 which draws gas from the vessel 6 and passes it through a further tube 9 back to the chamber 1 again through a sealing means 14.

A pressure control means 15 allows the pressure in the system to be held at any required level by venting gas to atmosphere or admitting gas into the system from a suitable source, eg a gas cylinder via a pressure regulator.

In operation the pump reduces the pressure in the refrigerated vessel 6, which causes vapour 4 to be drawn into the vessel 6 together with some gas. The temperature of the vessel 6 is maintained at a low enough value to condense the vapour, and any permanent gas passes through the vessel into the pump 7. Gas extracted by the pump 7 could be discharged to the atmosphere because it has been stripped of undesirable vapours in the refrigerated vessel 6 or, as in this illustration, may be recirculated to continue to evaporate the sample.

What is claimed is:

1. A method of reducing loss of a sample from a sample container partially open to atmosphere and containing the sample and a mix of solvent and liquid trifluoroacetic acid (TFA mix), said loss being due to creeping of TFA with its sample up the wall of the container, in which the top of the container includes a central, downwardly extending and open entrance tube forming an annular space with the wall of the container, i.e. in the form of an unspillable inkwell, comprising the step of filling the container with TFA mix to a level below that of the lowest level of the entrance tube, so that TFA vapour occupies the entrance tube up to a level slightly above that of said lowest level of the entrance tube but can go no further if gas or air, displaced in the container by the TFA vapour, is trapped in said annular space around the entrance tube below the upper wall of the container surrounding the entrance tube, and so that there is no continuous path in the inside surface of the container wall, in contact with TFA vapour, up which the TFA liquid mix can creep.

2. A method according to claim 1 in which there are a plurality of containers comprising wells of a microtitre plate, further comprising the step of providing each well with a sealing cap, each cap incorporating a said unspillable inkwell.

3. A method of reducing loss of a sample from a sample container open to atmosphere and containing the sample and a mix of a solvent and liquid trifluoroacetic acid (TFA mix) said loss being due to creeping of TFA with its sample up the walls of the container, comprising the steps of continuously removing TFA vapour from the sample container containing the sample and TFA mix, inserting a tube into the container to a position at which its lower open end is just above the TFA mix, and the top end of the tube is connected to a pump or reduced pressure collecting device, so as to suck out the TFA vapour as soon as it reaches the level of the lower end of the tube, and admitting an inert gas or air to the top of the container to compensate for the loss of gas volume caused by the removal of the TFA vapour.

4. A method of reducing loss of a sample from a container partially open to atmosphere and containing the sample and a mix of a solvent and liquid trifluoroacetic acid (TFA mix) said loss being due to creeping of TFA with its sample up the wall of the container, comprising the steps of forming the top of the container with a central, downwardly extending and open entrance tube which forms an annular space with the wall of the container, and placing the sample in the container with an atmosphere of an inert gas having a higher density than TFA vapour, and filling the container with said inert gas shortly before, or shortly after, adding the TFA to the container, so that said inert gas is not so readily displaced as air or nitrogen and prevents or delays the TFA vapour from filling the container which, in turn, prevents the liquid TFA mix from reaching the top of the container or delays the process sufficiently to prevent sample loss or cross-contamination arising from creep of TFA mix.

5. A method of reducing loss of a sample from a sample container partially open to atmosphere and containing the sample and a mix of a solvent and liquid trifluoroacetic acid (TFA mix), said loss being due to creeping of TFA with its sample up the wall of the container, including the steps of forming the top of the container with a central, downwardly extending and open entrance tube which forms an annular space with the wall of the container, filling the container with a heavy gas, and maintaining the heavy gas under a pressure greater than atmospheric pressure so that the possibility of the heavy gas being displaced by TFA mix vapour is reduced.

6. A method of reducing sample loss from a plurality of sample containers in the form of wells of a microtitre plate in a centrifugal evaporator, the wells containing the sample and a mix of a solvent and liquid trifluoroacetic acid (TFA mix), comprising the steps of:

(a) providing sealing caps for sealingly fitting to the tops of the wells, there being one cap for fitting to each well;

(b) connecting the caps to a closure plate;

(c) attaching a plurality of push rods to the closure plate, the rods passing slidingly through holes in the microtitre plate, said holes being located between wells and matching the positions of the rods on the closure plate, so that the rods protrude below the base of the microtitre plate and support the latter, when the caps are fitted to the wells and the evaporator is stationary;

(d) as soon as the TFA mix had been added to the wells, fitting the caps to the wells by applying the closure plate over the microtitre plate, whereby the TFA vapour evaporates in each well and forms a layer over the liquid surface but cannot fill the rest of the empty space above the liquid; and (e) subjecting the microtitre plate to centrifugal force in a swiveling member of the evaporator such that the microtitre plate is slidingly forced outwards relative to the pushrods to release the caps from the wells and allow evaporation to proceed.

* * * * *